United States Patent [19]

Baylor et al.

[11] Patent Number: 5,424,211
[45] Date of Patent: Jun. 13, 1995

[54] COMPOSITION FOR DETECTING URANYL

[75] Inventors: Lewis C. Baylor, North Augusta, S.C.; Susan M. Stephens, Athens, Ga.

[73] Assignee: The United States of America as represented by the United States Department of Energy, Washington, D.C.

[21] Appl. No.: 243,317

[22] Filed: May 16, 1994

[51] Int. Cl.⁶ ............................................. G01N 21/00
[52] U.S. Cl. ................................... 436/8; 436/58; 436/73; 436/164; 436/903; 436/904
[58] Field of Search ................ 436/58, 73, 164, 903, 436/904, 8, 18, 19

[56] References Cited

U.S. PATENT DOCUMENTS

| | | | |
|---|---|---|---|
| 3,099,537 | 7/1963 | Mason et al. | 23/230 |
| 3,403,004 | 9/1968 | Jungreis et al. | 23/230 |
| 4,320,093 | 3/1982 | Volesky et al. | 423/6 |
| 4,349,350 | 9/1982 | Fitoussi et al. | 23/230 |
| 4,511,660 | 4/1985 | Lubbers et al. | 436/163 |

OTHER PUBLICATIONS

Kanicky, V. et al. "The reaction of uranyl (2+) ion with chromazurol S and the spectrophotometric determination of uranium in the presence of Septonex." Collect. Czech. Chem. Comm. (1980), 45(5), 1525–54.

S. B. Savvin, Analytical Use Of Arsenazo III, Tatana 1961 vol. 8, pp. 673 to 685, Apr. 20, 1961.

S. B. Savvin, Photometric Determination Of Thorium and Uranium With Arsenazo III Reagent, Apr. 15, 1959.

Primary Examiner—David A. Redding
Attorney, Agent, or Firm—Brian R. Tumm; Harold M. Dixon; William R. Moser

[57] ABSTRACT

A composition for detecting the presence and concentration of a substance such as uranyl, comprising an organohalide covalently bonded to an indicator for said substance. The composition has at least one active OH site for forming a complex with the substance to be detected. The composition is made by reacting equimolar amounts of the indicator and the organohalide in a polar organic solvent. The absorbance spectrum of the composition-uranyl complex is shifted with respect to the absorbance spectrum of the indicator-uranyl complex, to provide better spectral resolution for detecting uranyl.

20 Claims, 2 Drawing Sheets

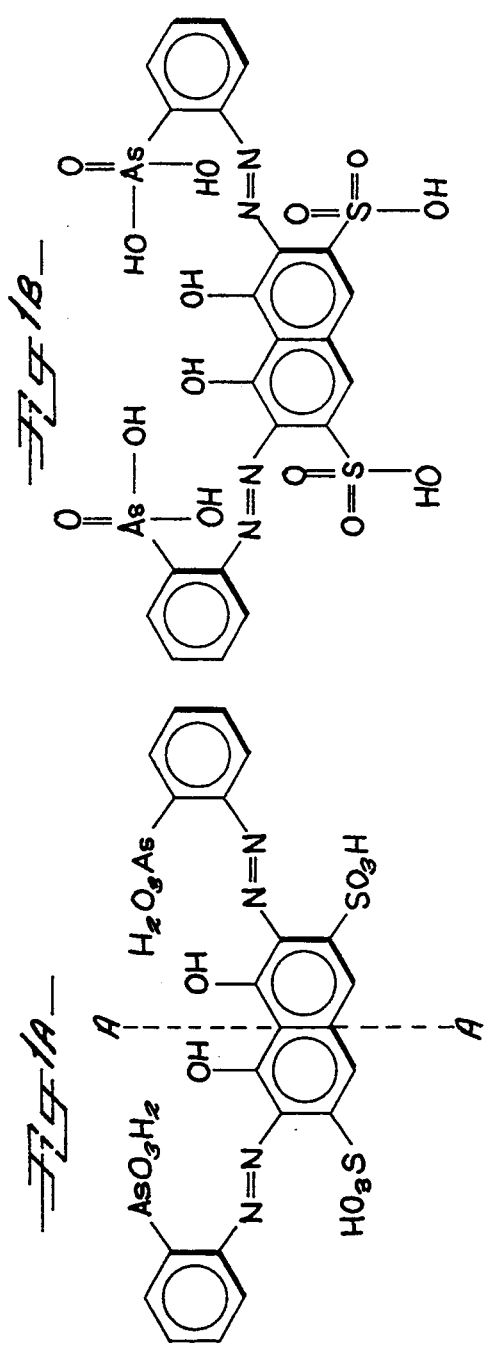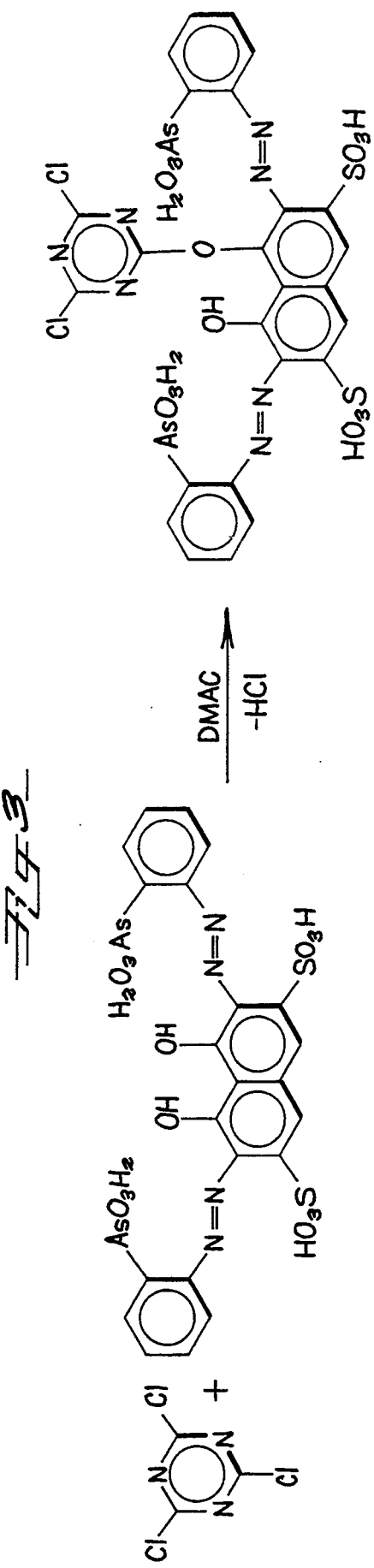

COMPOSITION FOR DETECTING URANYL

BACKGROUND OF THE INVENTION

1. Field of the Invention

The present invention relates to an indicator composition for use in spectrophotometric detection of a substance in a solution, and a method for making the composition. In particular, the invention relates to an indicator composition formed by covalently bonding an indicator to an organohalide. The indicator composition is also an indicator and is a better indicator than the indicator from which it is made, because, when it interacts with the substance of interest, better spectral resolution is obtained. The United States Government has rights in this invention pursuant to Contract No. DE-AC09-89SR18035 between the U.S. Department of Energy and Westinghouse Savannah River Company.

2. Discussion of Background

Optical indicators are used to detect the presence and concentration of chemical compounds in solutions. Useful indicators are sensitive to the particular substance being measured, but are unaffected by the fluid and other chemical species that may be present in the fluid. A large number of optical indicators are known, offering a wide range of choices for the detection and analysis of their corresponding analytes. As used herein, the terms "analyte," "analyte of interest" and "substance of interest" mean a substance whose presence and whose concentration is the focus of investigation. The terms "indicator" and "optical indicator" mean compounds that interact with the substance in such a way as to have different optical characteristics compared to the indicator in the absence of the substance. Examples of analytes that can be detected with optical indicators include oxygen, carbon dioxide, hydrogen ion concentration (pH), metals and metal ions, oxidation-reduction potential, electrolytes, glucose, and organic compounds (gasoline, benzene, trichloroethylene, toluene, xylene, pesticides, etc.).

Indicators are used in several ways. For example, fluorescence and absorbance indicators may be mixed with a sample of the solution to be tested. Then, the difference intensity between the light incident on the sample and light transmitted through, reflected, or emitted from the sample is measured. Measurements may be made at a single frequency, several frequencies, or a range of frequencies to obtain a spectrum. The difference between the measurements represents the interaction between the indicator and the analyte or group of analytes present in the sample. Both fluorescence indicators and absorbance indicators form a chemical complex with the analyte, resulting in a color change and a shift in the fluorescence or absorption spectrum of the sample. The term "absorption" as used herein means the decrease in the intensity of light passing through a fluid sample as the result of the interaction of the incident light and the sample. Typically, a single indicator is used to measure a single analyte, however, Luebbers, et al. (U.S. Pat. No. 4,511,660) make two, sequential measurements of the pH of a solution using two different indicators, then use the differences in measured pH to generate a signal related to the ion concentration of the solution.

One of the more recent uses of indicators is with optical sensing devices. An indicator, often in combination with a sample-permeable matrix, is positioned to interact with a test sample or process stream. Light is transmitted to the indicator by an optical fiber; the interaction between the indicator and the substance to be detected alters the light transmitted through the sample prior to its receipt by a receiving fiber. The indicator-analyte complex may absorb, reflect, refract, scatter, or fluoresce in response to the incident light. The concentration of the substance can be determined by comparing the received light to the transmitted light.

Alternatively, a substrate such as paper or glass can be coated with the indicator and then placed in contact with the solution to be tested. Indicators may be incorporated into a glass or polymer matrix to form an insoluble, re-usable composite, such as those described in the following commonly-assigned patent applications: "Optical Apparatus and Method For Sensing Uranyl" Ser. No. 08/189,823, filed Feb. 1, 1994; "Tetraethyl Orthosilicate-Based Glass Composition and Method" (Ser. No. 07/999,338, filed Dec. 31 1992). These so-called "bound indicators" are in an insoluble form, and are therefore more useful for industrial and laboratory applications because they can be used repeatedly. In many applications, the indicator is placed on or near the surface of an optical fiber, and the interaction between the indicator and the solution is monitored via the optical signals carried by the fiber to a detector.

Optical indicators are used to measure the uranium concentration of process solutions in facilities for extracting uranium from ores, production of nuclear fuels, and reprocessing of irradiated fuels. For example, Fitoussi, et al. (U.S. Pat. No. 4,349,350) determine U(VI) concentration in an organic solvent from the optical density of a mixed U(VI)-dialkyl dithiophosphoric acid-organophosphorus compound complex. Volesky, et al. (U.S. Pat. No. 4,320,093) use a microbe (Rhizopus arrhizus) to separate uranium from a solution and measure uranium concentration by using arsenazo III as a color developing agent for chelate complexes of U(IV). Jungreis, et al. (U.S. Pat. No. 3,403,004) react p-dimethylaminoaniline hydrochloride with salicylaldehyde, then react the reaction product with ammonia to produce a reagent that will complex with U(VI) to form $(UO_2Cl_4)^{-2}$. Mason, et al. (U.S. Pat. No. 3,099,537) treat organic solvents containing uranium with a colorimetric agent (ammonium thioglycollate).

Presently-available absorbance indicators, including uranium-sensitive absorbance indicators, frequently have limited sensitivities due to poor resolution between the absorbance spectra of the indicator and the chemical complex formed by the indicator and the substance or analyte to be detected. In addition, spectral analysis may be complicated by the presence of other compounds that complex with the indicator and interfere with the analysis. A satisfactory indicator composition should be easily prepared, chemically stable, sensitive to low concentrations of the substance of interest, and have short response time and good separation between the absorbance spectra of the indicator and the indicator-analyte complex.

SUMMARY OF THE INVENTION

According to its major aspects and broadly stated, the present invention is a composition for "indicating," or detecting, the presence and concentration of a substance in a solution, and a method for making the composition. The composition comprises an organohalide covalently bonded to ant indicator for the substance, in such a manner that the product is itself an indicator that provides increased spectral resolution for detecting the substance.

An important feature of the present invention is the fact that the composition has OH sites for complexing with the analyte and that the organohalide requires only one of the OH sites of the indicator to bond with it. The indicator molecule is selected to have at least two active OH sites so that, when the organohalide is covalently bonded to one of these OH sites, the indicator-organohalide composition has at least one remaining, active OH site. Therefore, although the indicator-organohalide composition differs chemically and structurally from the indicator alone, the indicator retains its ability to form a complex with the substance. Furthermore, the absorbance spectrum of the complex formed by the composition and the analyte is shifted to a greater extent than that of the complex formed by the indicator and the analyte.

Another feature of the invention is the selection of the indicator and the organohalide. As noted above, the indicator is preferably arsenazo III and the organohalide is preferably cyanuric chloride. These form a composition that is ideally suited for detecting uranyl.

Still another feature of the invention is the method for making the composition. The indicator and the organohalide are dissolved into a solvent, preferably a polar organic solvent, where they react to form the product composition. The method makes use of readily available indicators, organohalides and solvents; the reaction may take place at room temperature and pressure so no special process conditions are needed.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1A shows the structure of the arsenazo III molecule in abbreviated form;

FIG. 1B shows the structure of the arsenazo III molecule in expanded form;

FIG. 3 shows the reaction of arsenazo III with cyanuric chloride to form a composition according to a preferred embodiment of the present invention;

DETAILED DESCRIPTION OF A PREFERRED EMBODIMENT

A composition for detecting the presence and concentration of a substance includes an indicator for that substance, and an organohalide covalently bonded to the indicator. Preferably, the indicator has at least two active OH sites, each site capable of forming a complex with the substance to be detected. The organohalide forms a covalent bond at one of the active OH sites, thus, the composition has at least one remaining active OH site available for forming a complex with the substance. In a preferred embodiment, the composition is prepared by reacting an arsenazo compound such as arsenazo III with cyanuric chloride in dimethylacetamide (DMAC).

Chromotropic acid-based dyes which contain the arsenous group ($AsO_3H_2$), known as arsenazo compounds, are widely used as indicators for pH measurement and photometric detection of various elements. The arsenazo compounds form stable complexes with cations of the elements to be detected, enabling detection of these elements in strongly acid solutions and in the presence of other complex-forming ions such as sulfates, phosphates, fluorides, oxalates and the like. For example, arsenazo I, arsenazo II and arsenazo III are indicators for uranium ($U^{IV}$ and uranyl ($U^{VI}$)), thorium, the transuranium elements, the rare earths, iron, copper, lead, calcium, magnesium and barium. The selectivity of the arsenazo compounds for a particular element depends on the pH of the sample solution: in strongly acid solutions, color reactions occur more readily with elements whose ions readily tend to hydrolyze, such as $U^{IV}$; in weak acid solutions, with uranyl, iron III and the rare earths; in neutral solutions, with calcium and magnesium.

Figure 2:
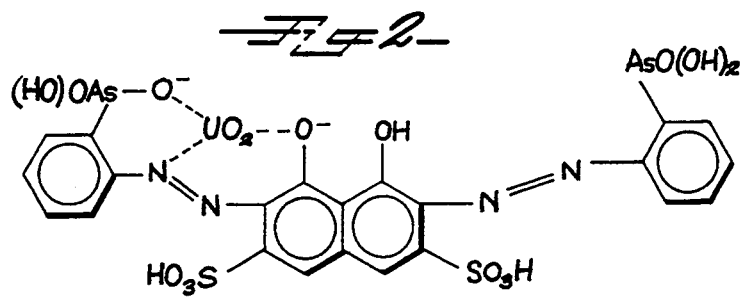
FIG. 2 shows the arsenazo III-uranyl complex.

Arsenazo III (2,2'-(1,8-dihydroxy-3,6-bisulfo-2,7, naphthalene)bis(azo)dibenzene) forms a highly stable complex with uranyl and other substances. As seen in FIG. 1A, the arsenazo III molecule has two $H_2O_3S$ groups, two arsenous groups and two OH groups, each group bound to a carbon atom in a ring to form a structure having mirror-image symmetry about a line A—A. This structure, shown in expanded form in Fig. 1B, has eight active OH sites and two functional $AsO_3H_2$—OH groups. The arsenazo III molecule forms a complex with a substance of interest by bonding a molecule of the substance to one of the functional groups. Both sides of the arsenazo III molecule are equally capable of forming a complex with the substance, however, only one side actually bonds a molecule of the substance thereto. By way of example, when arsenazo III is used to detect uranyl, only one of the functional groups bonds with a uranyl molecule (FIG. 2). While the molecules that form a complex are not permanently bonded to each other, the complex shown in FIG. 2 is highly stable since the uranyl ion is electrically attracted to the arsenazo III molecule at three points (indicated generally by dotted lines). While not wishing to be bound by theory, it is believed that formation of a complex by bonding a uranyl ion to either of the two functional $AsO_3H_2$—OH groups changes the planetary electronic structure of both N=N bonds, preventing bonding of a second uranyl ion to the other functional group.

When used to detect a suitable analyte (or group of analytes), arsenazo III reacts with the analyte to form a stable complex that has a different absorbance spectrum from arsenazo III alone. By way of example, arsenazo III reacts with uranyl to form the stable, inner-complex product shown in FIG. 2. Bonding to the left-hand $AsO_3H_2$—OH group is shown, however, the uranyl ion can bond to either $AsO_3H_2$—OH group. Whether bonding occurs at the left or right-hand group, the absorbance spectrum of the arsenazo III-uranyl complex is the same. Since the change in the sample absorbance is proportional to the amount of uranyl bound to the arsenazo III, the concentration of uranyl in the sample can be determined through well-known absorbance analysis techniques. For example, the color of an aqueous solution of arsenazo III varies from pink in weak acid solutions to violet in basic solutions. However, in an acid solution of pH between approximately 1 and 4, arsenazo III changes from pink to green in the presence of uranyl (different color changes may be found at different pH levels, or with different analytes). Uranyl concentrations of approximately 0.5 μg/ml or higher can be detected visually; concentrations as low as approximately 0.01 μg/ml can be detected with a spectrophotometer. If desired, the pH of a sample solution can be maintained at a predetermined level by the use of a buffer such as monochloroacetic acid and its salts.

The stability of the arsenazo III-uranyl complex makes arsenazo III a useful indicator for uranyl. However, other cations in the sample may bond to one of the $AsO_3H_2$—OH functional groups and interfere with the analysis. In addition, measurement of low uranyl concentrations is difficult due to poor resolution between the absorbance peaks of the complex and arsenazo III alone.

It has been found that, surprisingly, covalently bonding an organohalide to one of the active OH sites of an indicator such as arsenazo III produces a composition having improved sensitivity for detecting uranyl and other substances. By improved sensitivity, it is meant that the product composition has greater spectral resolution for detecting the substance of interest, as will be described more fully below. In addition, bonding the organohalide to one of the active OH sites of the indicator is believed to prevent bonding other, potentially-interfering cations to the composition.

A composition according to the present invention was prepared by adding arsenazo III and cyanuric chloride ($C_3N_3Cl_3$) in powder form to dimethylacetamide ($CH_3CON(CH_3)_2$; DMAC). Arsenazo III was provided in the form of its disodium salt (a crystalline, dark red powder). Once dissolved, the arsenazo III and cyanuric chloride reacted to form the composition shown in FIG. 3.

Figure 4:
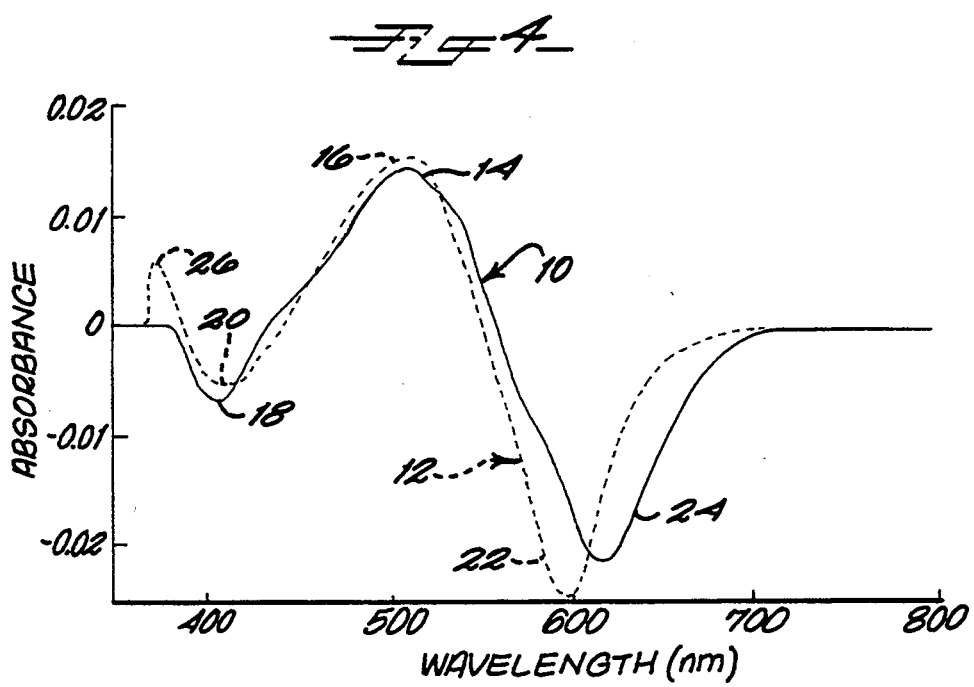
FIG. 4 shows the first derivative absorbance spectra of arsenazo III and the composition of FIG. 3.

FIG. 4 shows the first derivative absorbance spectra of arsenazo III and the reaction product. A spectrum 10 (arsenazo III) and a spectrum 12 (the above-described arsenazo III-cyanuric chloride composition) have absorbance peaks 14 and 16, respectively, at a wavelength of approximately 500 nm. Spectra 10 and 12 have absorbance minima 18 and 20, respectively, at approximately 400 nm. However, a minimum 22 of spectrum 12 is displaced from a corresponding minimum 24 of spectrum 10, and spectrum 10 has an additional peak 26, indicating that spectra 10 and 12 represent chemically and structurally different compounds.

The arsenazo III molecule gives up an H atom, and the cyanuric chloride molecule a Cl atom, as the cyanuric chloride forms a covalent bond at one of the active OH sites of the arsenazo III molecule. While it is believed that the reaction of arsenazo III and cyanuric chloride proceeds generally as shown in FIG. 3, an alternate reaction scheme involves formation of a covalent bond with cyanuric chloride at one of the $HO_3S$ sites. Bonding to the right-hand side of the arsenazo III molecule is shown in FIG. 3, however, it will be understood that bonding can occur at either side.

Although bound to cyanuric chloride, the arsenazo III molecule retains its sensitivity to those substances for which the free arsenazo III molecule is sensitive (pH, uranyl, etc.). That is, if the cyanuric chloride is bonded to arsenazo III as shown in FIG. 3, the arsenazo III-cyanuric chloride composition is capable of forming a complex with uranyl (and other substances of interest) at its remaining $AsO_3H_2$—OH functional group. If the cyanuric chloride is bonded to one of the $HO_3S$ sites, it is believed that the composition can form a complex with uranyl at only one of the $AsO_3H_2$—OH functional groups. Therefore, the composition can be used to detect the same analytes as arsenazo III (pH, uranyl, thorium, calcium, etc.), in a manner that is well known in the art.

The composition is preferably made by reacting approximately equimolar amounts of arsenazo III and cyanuric chloride in DMAC, however, other reagents and solvents may also be useful for the practice of the invention. By way of example, suitable solvents include those nonpolar organic solvents in which both the indicator and the organohalide are soluble, such as DMAC, other acetamides such as diethylacetamide and dipropylacetamide, ethyl acetate, the alcohols, and the ketones.

Other indicators having at least two active OH sites are suitable for use with the invention. As is known in the art, an active OH site (also known as a proton binding site) is an OH group bound to a carbon atom in a ring. Indicators with at least two active OH sites include the arsenazo compounds, bromocresol green (BCG) and chrome azurol S (CAS). For such an indicator, the reaction proceeds generally as follows:

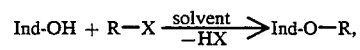

where Ind-OH represents the indicator, and R—X is an organohalide having a halogen atom X attached to a carbon chain R (carbon chain R may have a single carbon ring, or a plurality of carbon rings in a chain). Organohalides such as cyanuric chloride react with arsenazo III in acidic or neutral solutions; other organohalides react with arsenazo III in the presence of a weak base. Thus, the pH of the solvent may be adjusted to allow the reaction to proceed. Preferably, the organohalide is selected so that, when the organohalide is bonded to the indicator, at least one OH site is available for forming a complex with the substance of interest. In addition, the organohalide is selected so that the indicator-organohalide composition provides greater spectral resolution for detecting the substance than does the indicator alone.

Selection of the indicator and the organohalide may include analysis of their structures using well known chemical analysis techniques. For example, the structure of the indicator-organohalide complex may be computed from the structures of the indicator and the organohalide, and used to predict the optical absorbance properties of the complex. Alternatively, the optimum indicator and organohalide may be selected based on a modest amount of experimentation for each particular application.

In use, the composition is mixed with the fluid sample to be tested, for example, a sample that contains a quantity of uranyl ions or some other analyte of interest. The uranyl ions react with the composition to form a complex (hereinafter, the composition-uranyl complex), at a rate proportional to the uranyl concentration of the sample. The composition-uranyl complex alters the absorbance characteristics of the sample, allowing the uranyl concentration to be determined using known optical analysis techniques.

Figure 5:
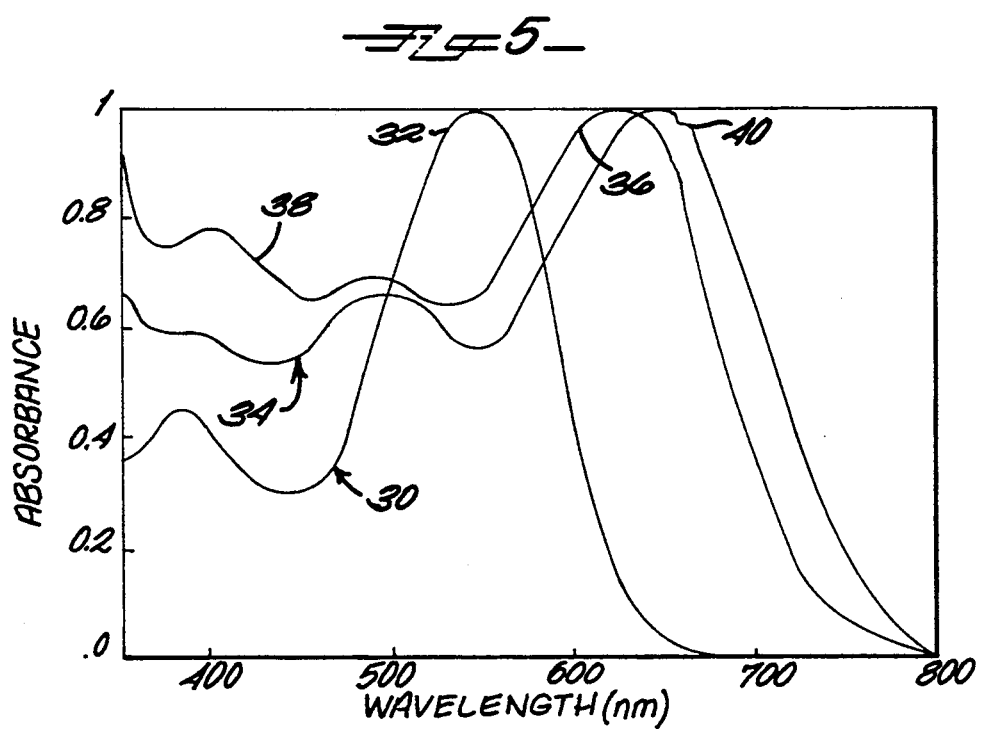
FIG. 5 shows absorbance spectra of arsenazo III, the arsenazo III-uranyl complex, and the composition-uranyl complex.

The above-described indicator composition was mixed with a uranyl-containing sample. The composition reacted with the uranyl ions in the sample to form a stable, inner-complex reaction product, and the absorbance spectrum of the sample was measured. FIG. 5 shows absorbance spectra of arsenazo III, a first complex formed by uranyl and arsenazo III, and a second complex formed by uranyl and the arsenazo III-cyanuric chloride composition. The spectra were measured over a wavelength range from approximately 350 to 800 nm using an ultraviolet-visible diode array spectrophotometer.

A reference spectrum 30 of an arsenazo III solution was measured prior to mixing the solution with a fluid sample containing uranyl ions. Spectrum 30 has a reference absorbance peak 32 at approximately 550 nm. A spectrum 34 represents the absorbance of the arsenazo III-uranyl complex, with an absorbance peak 36 at approximately 628 nm. A spectrum 38 represents the absorbance of the composition-uranyl complex, with an absorbance peak 40 at approximately 670 nm. Compared to peak 36, peak 40 is shifted further towards the longer-wavelength region of the spectrum with respect to reference peak 32. That is, the wavelength difference between peak 40 and reference peak 32 is greater than the wavelength difference between peak 36 and peak 32. Thus, the composition provides improved spectral resolution of peaks 38 and 32 and, therefore, easier determination of the uranyl concentration of the sample. As previously discussed, the shift in the absorbance spectrum of the composition-uranyl complex is attributable to the binding of cyanuric chloride to one of the active OH sites of the arsenazo III molecule.

FIG. 5 shows absorbance spectra each having a single distinct peak in the measured wavelength range (peaks 32, 36, 40). However, a different number of absorbance peaks might be measured for substances other than uranyl, absorbance spectra measured in a different wavelength range, or different compositions. Useful indicators generally form complexes having at least one absorbance peak in a suitable wavelength region for optical measurements.

The uranyl concentration of the sample may be computed by well known chemometric techniques, using calibration spectra for samples with known concentrations of uranyl. For example, Principal Component Regression (PCR) and Partial Least Squares (PLS) model spectral data sets by constructing orthogonal vectors to describe the variance between the spectra in the set. In PCR analysis, a model is built by decomposing the calibration spectra to a set of eigenvalues corresponding to each of the principal component regression vectors, and correlating the eigenvalues with the known concentrations. Once computed, the eigenvalues of this model can be related to the eigenvalues of an unknown spectrum by well known techniques such as multiple linear regression.

PLS analysis assumes a linear relationship between the data and the concentrations. An unknown spectrum is analyzed by computing likenesses between the spectrum and the orthogonal vectors of the calibration data set, then summing the contribution to the concentration from each of the vectors. Spectrum residuals are computed by subtracting the likenesses of the vectors from the original spectrum. The number of vectors used to describe a given data set is determined by minimizing the predicted error of a set of spectra with known concentrations. Whether PCR, PLS, or some other technique is used depends on the nature of the analyte to be detected and the instrumentation used.

As an example, the absorbance spectrum $A(v)$ is computed from the measured intensity of light transmitted through the sample:

$$A(v) = -\log_{10}(I(v)/I_0(v)),$$

where $I(v)$ is the intensity at a frequency $v$, and $I_0(v)$ is the blank intensity measurement. Using PCR, the concentration of an analyte such as uranyl may be found as follows:

1. Measure the spectra of a set of reference samples having a range of known uranyl concentrations to obtain S, a set of vectors that represents the spectra and their variations with uranyl concentration.
2. Take a first derivative, S', of S.
3. Decompose the set of S' into a set of orthonormal vectors V, where V represents spectral variations contained in the set S'.
4. Compute the dot product of S' with V: $E = S' \cdot V$.
5. The uranyl concentration C is related to E by the equation $C = f(E_i)$. For many substances of interest, C is a linear function of E, that is, $C = \Sigma A_i E_i + B$, where the constants $A_i$ and B are derived from a least squares fit of the computed values of $E_i$ versus concentration. For some analytes, $f(E_i)$ may assume some other form such as a polynomial, exponential, or some other type of function. Therefore, $f(E_i)$ is best determined by a modest amount of observation and experimentation for each particular analyte.

Once $f(E_i)$ is known, the concentration of the substance can be found as follows:

1. Measure the absorbance spectrum of the sample.
2. Compute the first derivative of the measured spectrum. If desired, second and higher-order derivatives may also be computed and used in the analysis.
3. Compute $E_i$.
4. Compute the concentration using the equation $C = f(E_i)$.

The above-described procedure may be used to compare a single measured spectrum with a calibration set for a single substance. If the sample solution contains more than one substance capable of forming a complex with the indicator, the analysis may include comparisons of the measured spectrum to calibration spectra for a variety of substances, in order to determine which of those substances are present in the sample and the concentration of each.

The sensitivity of a composition according to the present invention varies depending on the particular analyte, the test solution, and the selection of the indicator and organohalide used to prepare the composition. For example, the above-described arsenazo III-cyanuric chloride composition can be used to detect uranyl ion concentrations in the ppm range (as low as approximately 0.01 $\mu g/ml$). The composition forms a stable complex with uranyl, thus, it may be used to detect the presence and concentration of uranyl in a wide range of solutions, including aqueous solutions and organic solvents. In addition, the composition can be used to detect other analytes that can be detected with arsenazo III, including but not limited to cations of the transuranium elements and the rare earths.

It will be apparent to those skilled in the art that many changes and substitutions can be made to the preferred embodiment herein described without departing from the spirit and scope of the present invention as defined by the appended claims.

What is claimed is:

1. A composition for detecting the presence of a substance in a solution, said composition comprising:
   an indicator; and
   an organohalide covalently bonded to said indicator, said composition having at least one active OH site.

2. The composition as recited in claim 1, wherein said indicator has at least two active OH sites, and wherein said organohalide is covalently bonded to one of said OH sites.

3. The composition as recited in claim 1, wherein said indicator has at least two functional groups, each of said groups having at least one active OH site, each of said groups being capable of forming a complex with said substance, and wherein said organohalide is covalently bonded to one of said OH sites.

4. The composition as recited in claim 1, wherein said indicator is selected from the group consisting of the arsenazo compounds, bromocresol green and chrome azurol S.

5. The composition as recited in claim 1, wherein said indicator is arsenazo III.

6. The composition as recited in claim 1, wherein said organohalide is an organochloride.

7. The composition as recited in claim 1, wherein said composition is made by reacting said indicator with said organohalide in a polar organic solvent.

8. The composition as recited in claim 1, wherein said composition is made by reacting said indicator with said organohalide in a polar organic solvent, said solvent selected from the group consisting of the acetamides, ethyl acetate, the alcohols and the ketones.

9. A composition for detecting the presence of a substance in a solution, said composition comprising:
   an indicator having at least two active OH sites; and
   an organohalide having the formula R—X, where R is a carbon chain and X is a halogen atom, said organohalide covalently bonded to one of said OH sites of said indicator.

10. The composition as recited in claim 9, wherein said indicator has at least two functional groups, each of said groups being capable of forming a complex with said substance, each of said groups including at least one of said active OH sites.

11. The composition as recited in claim 9, wherein said indicator is selected from the group consisting of the arsenazo compounds, bromocresol green and chrome azurol S.

12. The composition as recited in claim 9, wherein said indicator is arsenazo III.

13. The composition as recited in claim 9, wherein said organohalide is cyanuric chloride.

14. The composition as recited in claim 9, wherein said indicator has the formula Ind-OH and said composition has the formula Ind-O—R, and wherein said composition is formed by the reaction $$\text{Ind-OH} + \text{R-X} \xrightarrow[-\text{HX}]{\text{solvent}} \text{Ind-O-R.}$$

15. The composition as recited in claim 9, wherein said composition is made by reacting said indicator with said organohalide in a polar organic solvent.

16. The composition as recited in claim 9, wherein said composition is made by reacting said indicator with said organohalide in a polar organic solvent, said solvent selected from the group consisting of the acetamides, ethyl acetate, the alcohols, the ketones, and mixtures thereof.

17. The composition as recited in claim 9, wherein said indicator is selected from the group consisting of the arsenazo compounds, bromocresol green and chrome azurol S, and wherein said composition is made by reacting said indicator with said organohalide in a polar organic solvent, said solvent selected from the group consisting of the acetamides, ethyl acetate, the alcohols, the ketones, and mixtures thereof.

18. A method for making a composition for detecting a substance in a solution, said method comprising the steps of:
   dissolving an indicator in a polar organic solvent, said indicator having at least two active OH sites; and
   dissolving an organohalide in said solvent so that said organohalide reacts with said indicator to form said composition, said composition having said organohalide covalently bonded to one of said OH sites of said indicator.

19. The method as recited in claim 18, wherein said dissolving steps further comprise .dissolving approximately equimolar amounts of said indicator and said organohalide in said solvent.

20. The method as recited in claim 18, wherein said indicator is selected from the group consisting of the arsenazo compounds, bromocresol green and chrome azurol S, wherein said solvent is selected from the group consisting of the acetamides, ethyl acetate, the alcohols, the ketones, and wherein said dissolving steps further comprise dissolving approximately equimolar amounts of said indicator and said organohalide in said solvent.

* * * * *